United States Patent [19]

Stephens

[11] Patent Number: 4,735,441
[45] Date of Patent: Apr. 5, 1988

[54] NON-LOOSENING LUER NUT

[75] Inventor: Thomas P. Stephens, Boxford, Mass.

[73] Assignee: Hewlett-Packard Company, Palo Alto, Calif.

[21] Appl. No.: 22,504

[22] Filed: Mar. 6, 1987

Related U.S. Application Data

[63] Continuation-in-part of Ser. No. 740,353, Jun. 3, 1985, abandoned.

[51] Int. Cl.$^4$ .............................................. F16L 19/00
[52] U.S. Cl. .................................. 285/175; 285/176; 285/332; 411/937.1
[58] Field of Search ................... 285/332, 175, 176; 411/417, 349, 437, 549, 263, 937.1, 938, 937, 937.2

[56] References Cited

U.S. PATENT DOCUMENTS

| 1,742,497 | 1/1930 | Dickinson | 285/332 X |
|---|---|---|---|
| 2,370,352 | 2/1945 | Hosking | 411/938 X |
| 2,507,535 | 5/1950 | Madsen | 285/176 X |
| 3,391,721 | 7/1968 | Rosan | 411/938 X |
| 3,456,704 | 7/1969 | Johnson | 411/937.1 X |
| 3,472,457 | 10/1969 | McAvoy | 285/332 X |
| 3,496,800 | 2/1970 | Brezinski | 411/937.1 X |
| 3,507,313 | 4/1970 | Stockslager | 411/937.1 X |
| 3,729,757 | 5/1973 | Wright | 411/937.1 X |
| 4,266,815 | 5/1981 | Cross | 285/332 X |
| 4,452,473 | 6/1984 | Ruschke | 285/332 X |

FOREIGN PATENT DOCUMENTS

| 1014454 | 7/1977 | Canada | 411/417 |
|---|---|---|---|
| 2822382 | 11/1979 | Fed. Rep. of Germany | 411/405 |
| 1194927 | 11/1959 | France | 285/176 |
| 264040 | 4/1929 | Italy | 285/176 |
| 394738 | 12/1965 | Switzerland | 285/175 |
| 635517 | 4/1950 | United Kingdom | 285/176 |

Primary Examiner—Thomas F. Callaghan
Attorney, Agent, or Firm—Donald N. Timbie

[57] ABSTRACT

An assembly for axially coupling male and female tubes including a nut having internal threads on a polygonally shaped inner surface at one end that can be screwed onto a projection on one of the tubes so as to draw a collar at the other end of the nut into axial contact with a shoulder on the other end of said tubes so as to draw the tubes together, the said projection being such as to ride in said threads at points along the surface of at least one side of said polygon so as to bend it outwardly from its unstressed position.

7 Claims, 1 Drawing Sheet

NON-LOOSENING LUER NUT

CROSS REFERENCE TO RELATED APPLICATION

This application is a continuation-in-part of application Ser. No. 06/740,353, filed 6/3/85, now abandoned.

BACKGROUND OF THE INVENTION

This invention relates to improvements in an assembly employing a hollow Luer nut to draw the ends of two hollow tubes together so as to form a continuous passageway therethrough. In this assembly, the outer end of a male tube becomes smaller towards an end thereof so as to form a conical surface that can be seated in an axial conical recess in an end of the female tube so as to form a sealed joint. An outer annular ridge or shoulder is formed adjacent to the larger end of the outer conical surface of the male tube, and an outer annular projection is formed about the end of the female tube. The Luer nut has an annular collar at one end and internal threads in the other, and does not deform during use. It is positioned with the male tube passing through the collar, the annular ridge on the male tube inside the collar, and the annular projection on the female tube engaging the threads. As the nut is screwed onto the annular projection, the collar contracts the ridge on the male tube and moves it toward the female tube until the conical end of the male tube is seated in the conical recess of the female tube so as to form a seal.

The normal Luer nut has a 10-pitch thread with 2 starts. Less than one turn of the nut is required to couple or decouple the tubes. Unfortunately, however, the nut is often loosened during normal handling or just relaxing and the seal broken. This is due to the high angular contact of the threads. The thread contact point is a steep wedge that is likely to unloosen because of the steep angle of contact. Some improvement was attempted by reducing the diameter of the threads as the interior of the nut was approached so as to increase the frictional torque as the nut was screwed into position. In some assemblies, however, the dimension of the threads in the nut and of the annular projection at the end of the female tube, although within normal manufacturing tolerances, were such that the frictional torque become too great for an operator to easily overcome before the male tube seated firmly enough in the female tube to form a seal. This is prevalent in a round female flange and is caused by the round shape of the nut being extended radially outward until the nut resists further radial expansion because the walls of the nut are in tension or hoop stress.

In assembling a tubing system with Luer nuts it is often desirable or even necessary to be able to rotate one tube with respect to the other without loosening the seal between the tubes. Such a situation may be encountered where one or both tubes being sealed is stiff, as, for example, when one or both are part of a molded valve. Not having an adequate seal can be life threatening, and an assembly in which this condition can be brought about without the technician being aware of it is therefore particularly dangerous.

BRIEF DESCRIPTION OF THE INVENTION

In accordance with this invention, the internal cross-section of the threaded section of the Luer nut is generally in the shape of a polygon that is deformable rather than stiff as in the prior art. In an axial view, the shape of the projection at the end of the female tube may be annular as in previous assemblies or it may have other shapes such as a rectangle. In any case, a portion of the periphery of the projection contacts one or more sides of the polygon. Wherever contact is made, the radial dimensions of the projection are such that the side is bent radially outward so that it acts like a spring and exerts a radially inward force on the projection. The resulting force of friction creates a frictional torque which does not prevent the operator from turning the nut, but which is sufficient to prevent the nut from becoming loose during normal use.

If the male tube is nearly seated in the female tube when the projection of the female tube reaches a point where the nut can be received onto it, male tube and female tube will be held very nearly in axial alignment so that the periphery of the projection may contact a side of the polygon at only one point. Otherwise, it would be necessary for the periphery to make contact with a number of sides of the polygon so that the female tube is held in axial alignment with the nut. The latter structure is preferable in our case, however.

In order to permit one tube to be rotated with respect to the other, without breaking a seal that has thus been formed between them, the rotational friction torque between the projection on one of the tubes and the sides of the polygon of the Luer nut is made to be greater than the rotational friction between the collar of the Luer nut and the ridge or shoulder of one of the tubes against which the collar bears when the seal is formed.

BRIEF DESCRIPTION OF THE DRAWINGS

FIG. 2 is an axial view of an assembly incorporating the invention in which the interior cross-section of the threaded portion of the Luer nut is generally triangular and the periphery of the projection at the end of the female tube is annular, FIG. 3 is an axial view of an assembly incorporating the invention in which the interior cross-section of the threaded portion of the Luer nut is generally triangular and the periphery of the projection at end of the female tube has two opposed arcs, and FIG. 4 is an axial view of an assembly incorporating the invention in which the interior cross-section of the threaded portion of the Luer nut is generally triangular and the periphery of the projection at the end of the female tube is approaching a square.

DETAILED DESCRIPTION OF THE INVENTION

Figure 1:
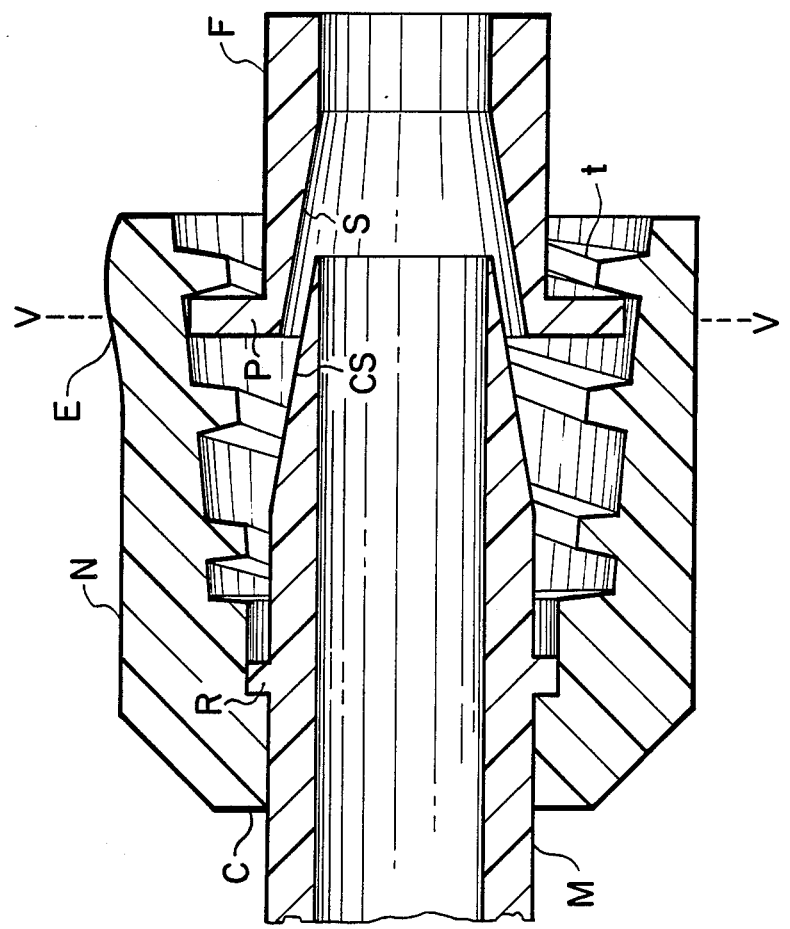
FIG. 1 shows what would be seen in an axial plane of a Luer nut assembly constructed in accordance with this invention at a point just before the male tube is seated in the female tube.

FIG. 1 illustrates what would be in an axial plane of an assembly incorporating preferred form of the invention. A hollow male tube M has a exterior conical surface CS and an annular ridge R adjacent the larger end of the surface CS. A hollow female tube F has an axial conical recess S into which the surface CS can be made to fit so as to form a seal and an outwardly extending projection P. A hollow Luer nut N is shown having a collar C at one end thereof and an internal thread t in the other end E that engages the projection P. As the nut N is rotated in one direction about its axis with respect to the female tube F, the projection P advances in the threads t and the female tube F is moved toward the male tube M. Finally, the conical surface CS and the conical recess S are seated as to form a seal.

In order to permit the tubes M and F to be rotated with respect to each other after a seal is formed between CS and S, the coefficient of friction between the surfaces of the collar C and the ridge R that are in contact is such that the rotational friction resulting from the actual force that is necessarily applied between them is less than the rotational friction between the projection P and the inner surface of the nut as well as threads t. This makes it possible to rotate the male tube M with respect to the female tube F without breaking the seal.

The flare or taper of the inner surface nut N at the end remote from the collar C is for the purpose of permitting projections P of different radial dimensions to immediately engage the threads t.

Reference is now made to FIG. 2 which illustrates what is seen in an assembly in a plane that is perpendicular to the axis of the female tube F and which passes through the projection P. Inasmuch as FIG. 1 is in itself a section, FIG. 2 is not a section of FIG. 1 but would be located at VV therein. In FIG. 2, the internal cross-section of the end E of the nut N is a polygon generally in the form of an equilateral triangle T. The projection P is an annulus which contacts the midpoints of the inner sides of the triangle so as to bend the sides outward. The undistorted shape of the inner surface of the triangle T is shown by a dash-dot line V. Although not in the plane shown in FIG. 2, the location of the threads t, when the sides of the triangle T are bent outward by the projection P, is shown by a dashed line. Where the periphery of the annular projection P contacts the sides of the triangle, it engages the threads t so that the nut N can be screwed onto the threads. The fact that the projection P is not engaged with the threads t at every point does not prevent this action from occurring.

An important aspect of this invention is the fact that wherever the periphery of the projection P on the female tube F contacts a side of the polygon formed inside the threaded end E of the nut, N its radial dimension is such as to bend the side outward. The side acts as a spring and creates a frictional torque sufficient to prevent the nut from being loosened during use.

In FIG. 2, the polygon formed by the internal cross-section of the end E of the nut N is an equilateral triangle t with rounded corners. Sharp corners could be used if desired. The periphery of the projection P is annular and is of such radius as to contact the central points of the sides of the triangle t and bend the sides outward from their unstressed position shown by the dashed line V. The bending can also be seen in FIG. 1 where the projection P contacts the inside of the threaded end E of the nut N.

In FIG. 3 the polygon formed by the internal cross-section of the end E of the nut N is an equilateral triangle T as in FIG. 2, but the periphery of the projection P' is formed by two arcs $A_1$ and $A_2$ on opposite sides of the axis of the female tube F and having that axis as a center, and by two parallel lines on either side of the axis and intersecting the arcs at corners $C_1$, $C_2$, $C_3$ and $C_4$. The central portion of the arc $A_1$ contacts the center of the top side of the triangle T, and the corners $C_3$ and $C_4$ respectively contact the other sides at points below the center. The sides are bent out at the points of contact so as to create the frictional torque required. The dash-dot line V is not shown.

FIG. 4 is the same as FIG. 3 except that the periphery of the projection P" is in the form of a square that contacts the triangular polygon T at its lower corners $C'_3$ and $C'_4$. The fact that the upper corners $C'_1$ and $C'_2$ do not initially contact the polygon presents no problem because the male and female tubes will stay substantially in alignment when they are nearly seated. Note, however, that the top side of the triangle T is not bent outward.

It is apparent that the outer surface of the end E of the nut N can have a cross-section that is shaped differently from that of its inner surface.

In order to increase the frictional torque as the nut is being screwed onto the external projection of the female tube, the radial dimensions of the polygon formed by the inner surface on which the threads are formed can be decreased as the interior of the nut is approached by an amount that is greater than that required to extricate the mold, but this should not be such as to cause binding.

What is claimed is:

1. A Luer nut assembly comprising
   a female hollow tube having an axis,
   a radial exterior projection at an end of said female tube, said projection having a given periphery in a plane perpendicular to the axis of the tube,
   means defining a conical recess in one end of said female tube,
   a male hollow tube having an external surface at one end thereof that is conical in shape so as to fit into said conical recess when the ends of said female and male tubes are axially drawn together,
   a shoulder formed on the exterior of said male tube at a point adjacent the lower end of said exterior conical surface,
   a Luer nut having a body, means defining a cavity in said body having an interior surface extending about an axis, threads formed on said interior surface, said interior surface having a cross-section in a plane perpendicular to said axis that is in the general form of a polygon, and which is enlarged as it approaches one end of said cavity,
   said nut having an inwardly extending collar at the other end of said cavity that is coaxial with said surface and through which said male tube passes, said collar being axially more remote from said one end of said cavity than said shoulder, and
   the dimensions and shape of the periphery of said projection being such that it contacts said interior surface of said cavity at at least one point.

2. An assembly as set forth in claim 1 wherein the periphery of said exterior projection is circular.

3. An assembly as set forth in claim 1 wherein the periphery of said exterior projection is rectangular.

4. An assembly set forth in claim 1 wherein the periphery of said exterior projection is in the form of parallel lines connected at opposite ends by curved lines.

5. A Luer Nut assembly comprising:
   a female tube having a recess within an end thereof;
   a male tube having an exterior surface at an end thereof that can form a seal when pressed into the recess of said female tube,
   a hollow Luer nut having an axis, an inwardly extending collar at one end thereof, and internal threads about said axis on an interior surface at the other end thereof, said internal surface having a cross-section in a plane perpendicular to said axis that is in the general form of a polygon, the sides of the nut forming said polygon being flexible, one said tubes having an exterior shoulder that can engage the inside of said collar, and the other one of said tubes having an exterior projection that can engage said internal threads at an intermediate point of at least one side of the polygon, the dimensions of said projection being such that it forces any side of the polygon with which it is in contact away from said axis so as to create a rotational friction force between such shoulder and said collar.

6. A Luer nut having a body means defining a cavity in said body having an interior surface extending about an axis, threads formed on said interior surface, said interior surface having a cross-section in a plane perpendicular to said axis that is in the general form of a polygon, and which is enlarged as it approaches one end of said cavity, an inwardly extending collar at the other end of said cavity that is coaxial with said surface.

7. A Luer nut as set forth in claim 6 wherein said threads are adapted to provide a given amount of friction torque with a projection on a tube screwed therein and said collar to be adapted to produce less frictional torque with a ridge on a tube inserted therethrough.

* * * * *